US008884085B2

(12) United States Patent
Van Rooijen et al.

(10) Patent No.: US 8,884,085 B2
(45) Date of Patent: Nov. 11, 2014

(54) CATALYTIC OXYCHLORINATION

(75) Inventors: Franciscus Edwin Van Rooijen, Zeist (NL); Arie De Bruijn, Uitgeest (NL); Jelle Johan Nieuwland, Purmerend (NL)

(73) Assignee: Albemarle Netherlands B.V. (NL)

( * ) Notice: Subject to any disclaimer, the term of this patent is extended or adjusted under 35 U.S.C. 154(b) by 1595 days.

(21) Appl. No.: 12/064,066

(22) PCT Filed: Aug. 16, 2006

(86) PCT No.: PCT/EP2006/065349
§ 371 (c)(1),
(2), (4) Date: Nov. 3, 2008

(87) PCT Pub. No.: WO2007/020268
PCT Pub. Date: Feb. 22, 2007

(65) Prior Publication Data
US 2009/0054708 A1    Feb. 26, 2009

(30) Foreign Application Priority Data

Aug. 18, 2005  (EP) .................................... 05107598

(51) Int. Cl.
| | | |
|---|---|---|
| *C07C 17/00* | (2006.01) | |
| *B01J 8/18* | (2006.01) | |
| *B01J 8/34* | (2006.01) | |
| *C07C 17/156* | (2006.01) | |
| *B01J 8/00* | (2006.01) | |
| *B01J 27/122* | (2006.01) | |
| *B01J 27/138* | (2006.01) | |
| *B01J 27/128* | (2006.01) | |
| *B01J 23/83* | (2006.01) | |

(52) U.S. Cl.
CPC ...... *B01J 27/122* (2013.01); *B01J 2208/00415* (2013.01); *B01J 2208/00407* (2013.01); *B01J 27/128* (2013.01); *B01J 2208/0053* (2013.01); *B01J 2208/0084* (2013.01); *B01J 2208/00061* (2013.01); *B01J 8/1872* (2013.01); *B01J 8/34* (2013.01); *C07C 17/156* (2013.01); *B01J 2208/00176* (2013.01); *B01J 2208/00681* (2013.01); *B01J 8/0055* (2013.01); *B01J 23/83* (2013.01); *B01J 27/138* (2013.01); *B01J 2208/00548* (2013.01)
USPC .......................................................... 570/225

(58) Field of Classification Search
None
See application file for complete search history.

(56) References Cited

U.S. PATENT DOCUMENTS 3,892,816 A * 7/1975 Kister ............................ 570/245
4,230,668 A * 10/1980 Sheely et al. ................. 422/140
(Continued)

FOREIGN PATENT DOCUMENTS

| EP | 0 931 587 A1 | 7/1999 |
| GB | 1 100 437 A | 1/1968 |

(Continued)

*Primary Examiner* — Clinton Brooks
(74) *Attorney, Agent, or Firm* — James A. Jubinsky; Marcy M. Hoefling; Nathan C. Dunn

(57) ABSTRACT

A process is disclosed for the catalytic oxychlorination of an olefin. In the process a feed containing the olefin, $O_2$ and HCl is contacted with an oxychlorination catalyst. The $O_2/2HCl$ ratio in the feed is in the range of from 0.50 to 0.58. Catalyst compositions for use in the oxychlorination reaction, in particular the oxychlorination of ethylene, are also disclosed. The catalyst compositions are in the form of particles suitable for use in fluid bed reactors, in particular baffled fluid bed reactors. Preferred catalyst materials comprise from 5.5 wt % to 14 wt % Cu. They may further comprise an earth alkali metal, such as Mg, and/or a rare earth metal. Preferred compositions contain less than 1 wt % of an alkali metal, which preferably is K.

17 Claims, 2 Drawing Sheets

(56) References Cited

U.S. PATENT DOCUMENTS

| | | | |
|---|---|---|---|
| 4,382,021 A | 5/1983 | Laurer et al. | |
| 4,446,249 A * | 5/1984 | Eden | 502/225 |
| 4,681,674 A * | 7/1987 | Graven et al. | 208/59 |
| 4,861,562 A | 8/1989 | Rowe | |
| 4,947,803 A | 8/1990 | Zen | |
| 5,382,726 A | 1/1995 | Young et al. | |
| 5,986,152 A | 11/1999 | Muller et al. | |
| 2002/0007097 A1 | 1/2002 | Walsdorff et al. | |

FOREIGN PATENT DOCUMENTS

| | | |
|---|---|---|
| GB | 1189815 | 4/1970 |
| JP | 11090233 | 9/1997 |
| WO | WO 2005/046866 A2 | 5/2005 |

\* cited by examiner

CATALYTIC OXYCHLORINATION

BACKGROUND OF THE INVENTION

1. Field of the Invention

The present invention relates to a process for the catalytic oxychlorination of ethylenically unsaturated hydrocarbons. The catalysts used in the process are designed for use in fluidized bed reactors, and are capable of providing high conversion rates and high selectivity, while avoiding problems due to stickiness.

Oxychlorination catalysts are well known. The most common oxychlorination reaction is the conversion of ethylene to ethylene dichloride (dichloroethane). Ethylene dichloride (EDC) is an intermediate to vinylchloride, which itself is the monomer for polyvinylchloride (PVC).

The oxychlorination reaction of ethylene is described by the following equation:

$$C_2H_4 + \tfrac{1}{2}O_2 + 2HCl \rightarrow C_2H_4Cl_2 + H_2O$$

Various options are available for carrying out this reaction. Air may be used as the source of oxygen, or oxygen, either by itself or mixed with an inert gas, may be used. Also, the reaction may be carried out in a fixed bed or in a fluid bed reactor. Fluid bed reactors are preferred.

Fluid bed reactors use catalysts based on copper salts, preferably $CuCl_2$, on a support. The support has a particle size suitable for good fluidization. The support particles may consist of an alumina or various alumina silicates, with alumina being the preferred support material, gamma-alumina being most preferred.

In addition to copper salts the catalyst may contain salts of alkaline metals, alkaline earth metals, and rare earths.

A serious problem with fluidized bed catalysts of this kind is caused by a phenomenon referred to as "sticking". This term describes the propensity of catalyst particles to stick to each other. It will be appreciated that, when this happens on any significant scale, the fluid properties of the bed are disturbed. At the same time the free-flowing properties of the catalyst in cyclone devices used for separating entrained catalyst particles from the product stream are negatively affected. This results in significant amounts of catalyst being removed from the reactor by the flow of gases. Catalyst material thus entrained by the gas flow ends up in the quench unit that is installed downstream of the reactor. An increased amount of catalyst material in the cyclones is a tell tale sign to the alert operator that sticking might be occurring.

Sticking also leads to a reduced reaction rate, and thus a reduced conversion of reactants, which is evidenced by an increase in residual HCl. An increase in residual HCl in turn causes sticking to increase, which risks putting the reaction conditions into a vicious cycle.

An alert operator may be able to reverse the occurrence of sticking, provided it is detected early enough, by increasing the oxygen feed ratio and/or the reaction temperature. Both actions result in a higher conversion rate, which lowers the amount of residual HCl, but also results in increased oxidation to CO and $CO_2$ (jointly referred to as $CO_x$). Thus, the measures required to reverse sticking or to avoid sticking cause the product yield to decrease, and therefore carry a considerable cost.

Oftentimes it will not be possible to reverse an occurrence of sticking by adjusting the reaction conditions. It may be necessary to stop the reactor, clean it out, and start it back up. It will be appreciated that the phenomenon of sticking may cause serious damage to the economic operation of an oxychlorination reactor.

Although the phenomenon of sticking has been the subject of much discussion and many publications, it continues to be poorly understood. It is generally accepted that it is the copper in the catalyst that is responsible for "stickiness", that is, the propensity of catalyst particles to stick together. During the catalytic reaction the copper ions are reduced from Cu(II) to Cu(I), and again oxidized to Cu(II). It is generally believed that copper in its Cu(I) form is the main actor in the sticking phenomenon. The theory is that Cu(I) compounds, such as CuCl, are mobile or even liquid at the reaction temperature. According to this theory these mobile copper compounds migrate to the surface of the support particles and form liquid bridges with other such particles.

Based on this theory it has been suggested to form oxychlorination catalysts by co-precipitation of Cu ions and alumina. The copper ions in a co-precipitated catalyst are more strongly held in the alumina matrix than copper ions deposited on an alumina support by impregnation. One would expect co-precipitated catalysts to be less susceptible to sticking, and this is indeed the case. However, co-precipitated catalysts are less active than catalysts obtained by impregnation because the copper ions are less accessible to the reactants.

2. Description of the Related Art

EP 0 119 933 B1 discloses a different approach to reducing stickiness. The goal is to prepare an impregnated catalyst consisting of porous particles of which the surface layers are relatively poor in copper content. This is accomplished by also impregnating a solution of $MgCl_2$, and carrying out the impregnation in the presence of a strong acid. The copper content of the outer layers of the particles is determined by X-ray photoemission spectroscopy (XPS).

Because of the mobility of copper compounds it is unlikely that XPS could provide a meaningful picture of the presence of copper on porous support particles. Even if such a thing could be measured at ambient conditions, the result is of limited validity for the situation under reaction conditions, when the much more mobile Cu(I) compounds are formed and the temperature is much higher. If indeed the copper ions are preferentially located in the pores, away from the surface, one would expect the activity of the catalyst to suffer, as the copper ions are less available to partake in the catalytic reaction.

Yet another approach has been the use of promoters to increase the activity of the catalyst. U.S. Pat. No. 4,069,170 discloses supported catalysts comprising salts of copper, potassium, didymium (a mixture of rare earth metals, rich in La) Lanthanum, and optionally magnesium. The catalyst composition "does not cake and does not cause defluidization" (see Abstract of US '170). Although the disclosed catalyst composition contains from 0.5% to 15% $CuCl_2$, the specific examples without exception contain 5.3% or less $CuCl_2$. Also, all specific examples contain an amount of $DiCl_3$ that exceeds the amount of $CuCl_2$. In addition, these catalysts contain significant amounts of KCl and $LaCl_3$. Apparently, the approach taken is to reduce stickiness by lowering the amount of copper in the composition, and to compensate for the resulting loss in catalytic activity by adding significant amounts of promoter materials.

In spite of these efforts there continues to be a need for oxychlorination catalysts having copper as the main catalytically active metal, wherein the copper ions are fully accessible to the reactants, and that do not suffer from stickiness.

The problem of stickiness is particularly acute with catalysts designed for use in fluidized bed reactors comprising baffles. These baffled reactors differ from a conventional fluidized bed reactor in that they contain a number of perforated plates, placed at different heights in the reactor. As compared to conventional fluidized bed reactors, the residence time of the reactants in a baffled reactor is much shorter. This much shorter residence time requires a catalyst having a high activity. This high activity is typically attained by providing a catalyst having a relatively high copper loading. The preferred catalyst has the copper introduced to the catalyst by impregnation, rather than by co-precipitation with the support material. Using impregnation as the technique for introducing copper into the catalyst increases the activity of the catalyst, but also increases the risk of stickiness.

It is therefore an object of the present invention to provide a process using a copper-based oxychlorination catalyst having a high activity, while not being susceptible to stickiness. It is a further object of this invention to provide a catalyst suitable for use in a baffled reactor, without being susceptible to stickiness. In a preferred embodiment the catalyst is made by impregnating a support material with a solution of $CuCl_2$.

BRIEF SUMMARY OF THE INVENTION

The present invention relates to a process for the catalytic oxychlorination of an olefin with a gas comprising oxygen and HCl in an $O_2/2HCl$ ratio in the range of 0.50 to 0.58.

The process of the present invention uses an oxychlorination catalyst having a HCl conversion, as defined herein, of at least 99.4%; an EDC selectivity, as defined herein, of at least 98.5%; and a critical oxygen/hydrochloric acid ratio for stickiness, as defined herein, of not more than 0.52.

In a specific embodiment, the catalyst used in the process comprises a support material, which is a refractory oxide having deposited thereon from 5.5 to 14 wt % Cu. The catalyst may further comprise an earth alkaline metal, such as Mg. If the catalyst comprises an alkali metal, the amount is not higher than 1 wt %, preferably not higher than 0.6 wt %; the preferred alkali metal is K. The catalyst may further comprise a rare earth metal, or a mixture of rare earth metals, preferably in an amount of from 0.2 to 5 wt %.

Small amounts of Fe, typically less than 0.1 wt %, may be present in the catalyst compositions used in the process of the present invention. In a preferred embodiment the catalyst is designed for use in a baffled reactor.

BRIEF DESCRIPTION OF THE DRAWINGS

A specific embodiment of the invention will be explained with reference to the drawings, of which.

DESCRIPTION OF ILLUSTRATIVE EMBODIMENTS

Figure 1:
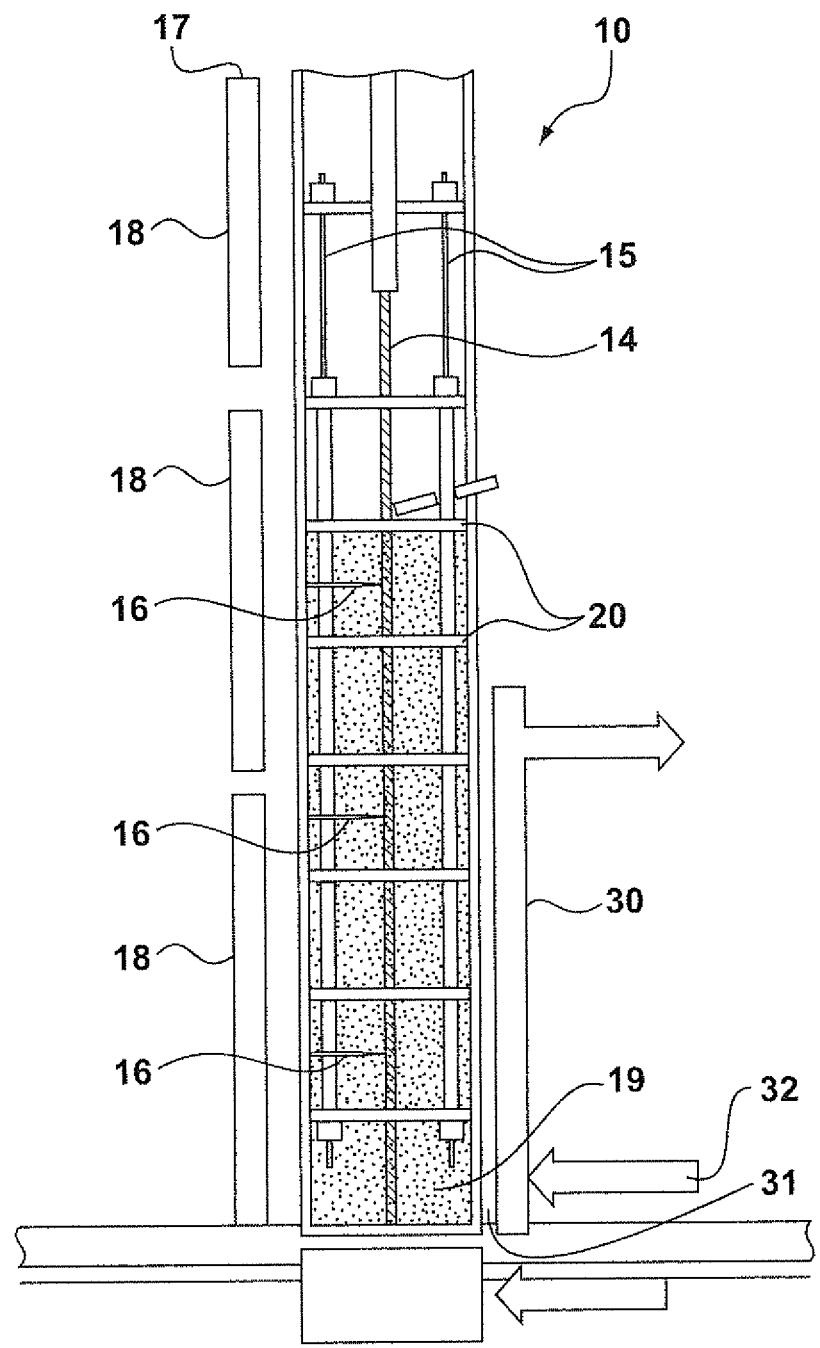
FIG. 1 is a schematic representation of a test reactor for testing catalyst materials.

The following is a description of certain embodiments of the invention, given by way of example only and with reference to the drawings Taking the oxychlorination reaction of ethylene as the model, this reaction is represented by the following equation:

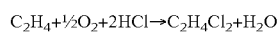

One might expect that the objective of the skilled person would be to maximize the conversion of ethylene, if necessary by providing an excess of $O_2$ and HCl in order to drive the reaction to the right hand side of the equation. In practice, there is an overriding need to maximize the conversion of HCl, because it is a highly corrosive gas, and its removal from the reactor effluent involves the consumption of caustic, which is an expensive material. The catalysts used in the process of the present invention provide a HCl conversion, as defined herein, of 99.4% or better.

EP 0 119 933 B1 focuses on the $HCl/C_2H_4$ ratio as the important parameter in determining stickiness. Indeed, below a HCl/ethylene ratio of 1.90 all tested catalysts showed good fluidization behavior, but the EDC yield was relatively poor. Increasing the HCl/ethylene ratio to more than 1.93 improved the EDC yield somewhat, but some of the tested catalysts started to show poor fluidization. With the better catalysts of this reference the EDC yield could be improved by further increasing the HCl/ethylene ratio, but then the HCl conversion dropped to less than 99.0%.

The present invention is based in part on the discovery that an important driver for stickiness behavior is the $O_2/2HCl$ ratio. This ratio is defined as two times the molar ratio of $O_2$ and HCl in the oxychlorination reaction feed. According to the reaction equation, the stoechiometric ratio is 0.50. It has now been discovered that a slight excess of $O_2$, i.e., an $O_2/2HCl$ ratio of 0.52 or greater, results in a dramatic improvement in HCl conversion. Preferably, the $O_2/2HCl$ ratio is at least 0.53, more preferably at least 0.54. It is desirable to avoid a greater excess of oxygen than is necessary to reach or approach maximum HCl conversion, as otherwise too much $CO_x$ might be formed. Preferably the $O_2/2HCl$ ratio will be kept at or below 0.58, more preferably at or below 0.56.

It has further been discovered that a slight excess of oxygen also prevents stickiness. In general, most catalysts will not suffer stickiness when the reactor is operated at a reaction temperature of 210° C. and an $O_2/2HCl$ ratio of 0.54 or higher. However, it should be recognized that both reaction temperature and $O_2/2HCl$ ratio are subject to fluctuations even in a carefully monitored reactor. The susceptibility to stickiness of certain catalysts has been found to increase dramatically as the $O_2/2HCl$ ratio approaches 0.50.

It is important to test catalyst materials under standardized conditions, at a reaction temperature of 210° C. and at decreasing $O_2/2HCl$ ratios. The $O_2/2HCl$ ratio at which stickiness for a specific catalyst is first observed is the critical $O_2/2HCl$ ratio for stickiness for that particular catalyst. If no stickiness is observed at a ratio of 0.50 the catalyst will be reported as having a critical ratio of <0.50.

The catalysts used in the process of the present invention have a critical $O_2/2HCl$ ratio for stickiness of not more than 0.52, preferably not more than 0.50.

The third important performance parameter of an oxychlorination catalyst of the present invention is the EDC selectivity, defined as the percentage of converted ethylene that is converted to EDC, determined at a reactor temperature of 210° C. and an $O_2/2HCl$ ratio of 0.54. The catalysts used in the process of the present invention have an EDC selectivity of at least 98.5%, preferably at least 99.0%.

The catalysts used in the process of the present invention are unique in that they simultaneously meet the following performance criteria:

1. HCl conversion at an $O_2/2HCl$ ratio of 0.54 and a reaction temperature of 210° C. of at least 99.4%, preferably at least 99.6%;
2. EDC selectivity at an $O_2/2HCl$ ratio of 0.54 and a reaction temperature of 210° C. of at least 98.5%, preferably at least 99.0%;
3. a critical $O_2/2HCl$ ratio for stickiness at a reaction temperature of 210° C. of not more than 0.52, preferably not more than 0.50.

The catalysts used in the process of the present invention comprise a carrier selected from the group of refractory oxides. The carrier is in the form of particles with a particle size suitable for use in a fluidized bed reactor. Specifically, the average particle size may be in the range of 40 to 80 microns, preferably from 60 to 80 microns. A preferred refractory oxide for use herein is an alumina, most preferred is gamma-alumina.

The catalysts further comprise one or more metal salts. Preferred are catalysts comprising a Cu salt, specifically $CuCl_2$. The amount of Cu (calculated as Cu) ranges from 5.5 wt % to 14 wt. %, preferably from 7.0 wt % to 11 wt. %, more preferably from 7.5 wt % to 10 Wt %.

The catalysts may further comprise promoter metal components, such as earth alkaline metals, alkali metals, and rare earth metals.

If an alkaline earth metal is present it is preferably present at a level of from 0.2 wt % to 5 wt %, more preferably from 1.0 wt % to 2.0 wt %, calculated as the metal. A preferred alkaline earth metal is Mg.

If a rare earth metal is present it may be present as one rare earth metal, or as a mixture of rare earth metals. Lanthanum-rich mixtures and cerium-rich mixtures are both suitable. Rare earth metals, if used, are typically present at a level of from 0.2 to 5 wt %, calculated as the metal.

Alkali metals are inherently present as contaminants of raw materials used in the preparation of the carrier or the entire catalyst. In particular Na is a common contaminant of many inorganic materials. The amounts of alkali metal introduced in this way are generally too small to have an appreciable effect on the performance of the catalyst. These contaminant levels are not included in reciting the composition ranges of the catalysts used in the process of the present invention.

Contrary to common belief, alkali metals have not been found to improve the performance of the catalysts used in the process of the present invention in a meaningful way. In addition, it has been found that significant levels of alkali metals in the catalysts used in the process of the present invention increase their susceptibility to stickiness.

Accordingly, the catalysts used in the process of the present invention comprise less than 1% alkali metal additive, calculated as the metal. If an alkali metal additive is used, the preferred alkali metal is K. It is preferred not to add Na to the catalyst compositions of the present invention.

The catalysts used in the process of the present invention are prepared by contacting carrier particles with aqueous solutions of salts of the metals to be incorporated in the catalysts. Contacting in this context may be a technique such as co-mulling, co-precipitation, impregnation, and the like. Impregnation is preferred, as it results in a greater availability of the metal ions. In particular incipient wetness impregnation is a suitable technique for contacting the carrier particles with the metal salt solution. The metal salts used in the preparation of the catalysts are preferably the chlorides.

It is desirable to mix all metal components in a single aqueous solution for introduction onto the carrier by incipient wetness impregnation. However, in incipient wetness impregnation the amount of fluid that may be used is determined by the pore volume of the carrier. Solubility limitations may make it impossible to introduce all metal components in a single impregnation step. In those cases it is possible to use two or more impregnation steps, separated by drying steps.

Catalyst Testing

Figure 2:
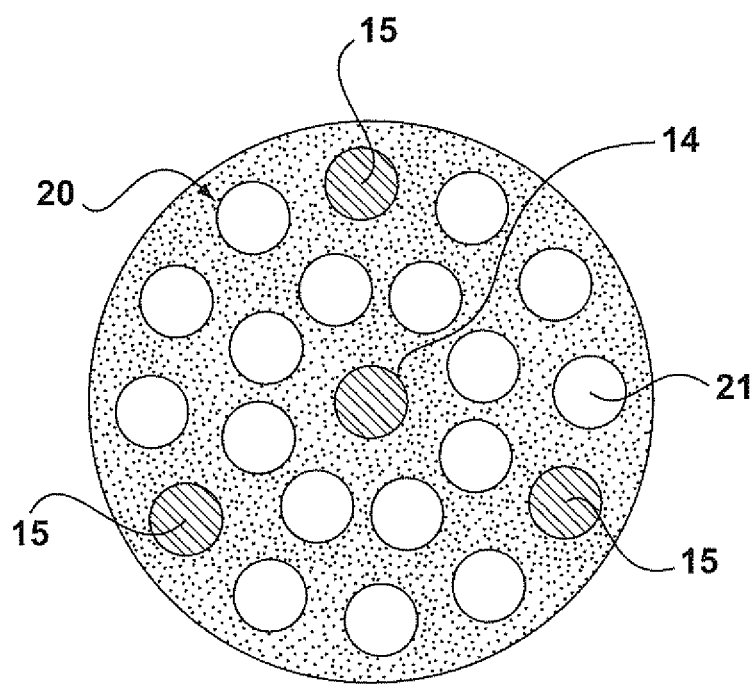
FIG. 2 is a top view of one of the baffle plates of the reactor of FIG. 1.

Catalyst samples were tested in a pilot scale reactor of the design as shown in FIG. 1. Reactor 10 is a glass tube having an inner diameter 11 of 38.1 mm, and a wall thickness 12 of 3 mm. Thermocouple 14 is mounted along the central axis of the reactor. Attached to thermocouple 14 are eleven baffle plates 20, the design of which is shown in detail in FIG. 2. The baffle plates, which are spaced 81 mm from each other, are connected to each other with steel tubes 15.

The baffle plates have a diameter of 37.5 mm, leaving a clearance of about 0.30 mm between the baffle plates and the wall of the reactor. The baffle plates are provided with holes 21, having a diameter of 5.4 mm. The number of holes is such that their combined surface area represents about 35% of the total surface area of a baffle plate (i.e., about 18 holes per baffle plate). The baffle plates are made of stainless steel.

Temperature probes 16 are placed at 10 mm, 110 mm, 210 mm, 410 mm, 710 mm, 1110 mm, 1410 mm and 1810 mm from the bottom of the reactor. Glass reactor tube 10 is wrapped with resistance heating wire 17, which is used for heating the reactor. The heating wiring is divided in four individual sections 18, which are controlled independently.

A second glass tube 30, having an internal diameter greater than the external diameter of the reactor, is placed around reactor tube 10, thus forming a cooling mantle 31. The reactor may be cooled by feeding a flow of cold air 32 (air temperature 20° C.) into cooling mantle 31. The air flow is controlled by means of an MFC (mass flow controller).

The combination of individually controlled heating sections 18 and cooling mantle 31 permits a high degree of control over creating and maintaining a desired temperature profile inside reactor 10.

Reactor 10 is charged with 450 ml of catalyst particles, creating a catalyst bed 19, with a height in rest of about 39 cm. When fluidized the height of the catalyst bed is about 55 to 60 cm. The weight of the catalyst is measured prior to its introduction into the reactor.

Reactants are fed into reactor 10 at the bottom, via preheater 32. Reaction products leave the reactor tube at the top, and enter a wider steel tube (not shown) mounted vertically on top of glass tube reactor 10. When the reactants enter this wider tube the flow rate of the reactants decreases, allowing entrained catalyst particles to fall back into the reactor. From the steel tube the reaction products enter a cyclone (not shown) where any remaining catalyst particles are separated from the reaction products.

The reaction mixture comprises HCl, ethylene, oxygen, and nitrogen. To ensure accurate metering of the reactants the feed lines are equipped with electronic mass flow controllers supplied by Rosemounts Brooks, type 5850S.

In a typical test the flow of HCl is fixed at a weight hourly space velocity (WHSV) of 12 mmol HCl/hr/kg catalyst. In function of this HCl flow the ethylene flow is fixed to the desired $C_2H_4/2HCl$ ratio (1.60 for the tests reported herein). Likewise, the oxygen flow is fixed to the desired $O_2/2HCl$ ratio. Finally, the nitrogen flow is fixed such that 40% of the reactant flow is nitrogen.

Determination of Reaction Conditions and Reaction Product Composition

After the reactants are admitted to the reactor adjustments are made to the heating and cooling settings until the temperature reading in the reactor at 110 mm from the bottom stabilizes at the desired value (210° C. in many of the experiments). After steady state is reached all receptacles of reaction products are readied for receipt of reaction products, and the reaction is allowed to run uninterrupted for three hours.

After leaving the cyclone the reaction products are led into a titration section. Here the reaction product mixture is bubbled through an aqueous liquid to absorb the unconverted HCl. Continuous titration is used to provide a real-time reading of the amount of HCl in the reaction product mixture.

Passage through the titration section cools the reaction product mixture to room temperature, at which EDC is in the liquid phase. Any remaining gaseous reaction products (mainly $CO_x$) are collected and analyzed with gas/liquid chromatography (GLC). The liquid reaction product is collected during the three-hour test run, and allowed to separate into a water phase and an EDC phase. The water phase is analyzed for any water-soluble reaction products (the water phase typically contains about 0.4% EDC).

There is one organic component that mainly dissolves in the water phase, and that is chloral. The EDC phase is separated from the water phase, and analyzed (a.o. for chloroform). Then the EDC is put back to the water phase, and caustic is added to convert the chloral to chloroform and sodium formiate. The chloroform dissolves in the EDC phase. Then, for the second time, the EDC is separated and analyzed. The difference in $CHCl_3$, compared to the first analysis, equals the amount of chloral.

The analyses of the reaction product mixture permit the calculation of HCl and $C_2H_4$ conversions and selectivities in the usual manner. The results are checked by determining a carbon balance and a chlorine balance, both of which must be between 98% and 102%, or the test will be discarded as unreliable.

Catalyst Stickiness

Catalyst stickiness is easily observed, as it results in a number of anomalies in the reaction behavior. Stickiness manifests itself in an increase in the amount of catalyst entrained by the reactants, as is visible as an increase in the amount of catalyst material collecting on the baffle plates in the upper part of the reactor and in the amount of catalyst material collected in the cyclone. In addition, the reactor bed becomes less homogenous, with large bubbles of reactant gases forming in the bed. Moreover, stickiness will result in an increase in unreacted HCl, which is easily detected as unreacted HCl is continuously measured by titration.

An easy and highly reliable indicator of stickiness is the presence of catalyst particles sticking to the wall of the glass reactor. An experienced operator will have no difficulty recognizing the occurrence of catalyst stickiness in the reactor.

Critical $O_2/2HCl$ Ratio for Stickiness

A test run is carried out as described above, with a reaction temperature of 210° C. and an $O_2/2HCl$ ratio of 0.56 [mole/mole]. If stickiness is observed during the three-hour test run the critical ratio is reported as being greater than 0.56.

If no stickiness is observed the test is repeated at the same reaction temperature (210° C.) and an $O_2/2HCl$ ratio of 0.54 [mole/mole]. If stickiness is observed the critical ratio is reported as greater than 0.54, but less than 0.56. The critical ratio may be determined more accurately be repeating the test at ratio 0.55.

If no stickiness is observed at ratio 0.54. the test is repeated at ratio 0.52. If stickiness is observed in this test the critical ratio is reported as greater than 0.52, but less than 0.54 (an additional test may be run at ratio 0.53 to further fine-tune the critical ratio).

If again no stickiness is observed at ratio 0.52, the test is repeated at ratio 0.50. If there still is no sign of stickiness the reaction temperature is quickly increased to 230° C. The sudden increase in reaction temperature results in an increase in unreacted HCl in the product flow, which tends to cause stickiness. If the increase in reaction temperature does not cause stickiness the catalyst is assigned a critical ratio of <0.50.

It has been found that this test for stickiness is highly predictive of the behavior of the catalyst in a commercial fluid bed reactor. The catalysts used in the process of the present invention have a critical $O_2/2HCl$ ratio for stickiness of not more than 0.52.

HCl Conversion

HCl conversion is defined as the percentage of HCl in the reactant mix that is converted during the reaction.

Most catalysts reach fill HCl conversion in a standard test run at 210° C. if the $O_2/2HCl$ ratio is 0.58 or greater. However, such a high ratio typically results in relatively poor EDC selectivity, because more undesirable by-products ($CO_x$ and chlorinated by-products) tend to be formed. It is desirable to formulate a catalyst that produces high HCl conversions at lower $O_2/2HCl$ ratios. The catalysts used in the process of the present invention reach an HCl conversion of at least 99.4% at a reaction temperature of 210° C. and an $O_2/2HCl$ ratio of 0.54.

EDC Selectivity

EDC selectivity is defined as the percentage of converted ethylene that is converted to EDC. As EDC is the desired product of the reaction, EDC selectivity is of great economic significance.

EDC selectivity tends to increase as the $O_2/2HCl$ ratio is decreased from, say, 0.60 to 0.50. However, for reasons explained above, it is not practical to operate a commercial reactor at $O_2/2HCl$ ratios at or near 0.50. A good practical compromise is operating a commercial reactor at a ratio of 0.54.

The catalysts used in the process of the present invention produce an EDC selectivity at 210° C. and an $O_2/2HCl$ ratio of 0.54 of at least 98.5%, preferably at least 99.0%.

The following catalysts were prepared at 5 kg scale in a laboratory tumble reactor. The reactor was equipped with a shell through which heated oil could be circulated for heating the contents of the reactor. The metal components were dissolved in water in the form of their chloride salts. The alumina carrier was impregnated with a volume of this aqueous solution corresponding to 115% of the pore volume of the alumina, which permitted the impregnation to be carried out in one step.

Impregnation was carried out at room temperature and atmospheric pressure. The impregnation step took about 7 minutes, after which the reactor was allowed to tumble at room temperature for another five minutes. Then the reactor was heated to 125° C., and kept at this temperature for 2 hours under continued tumbling. During the cooling step a light air flow was passed through the reactor.

The catalyst samples were tested as described above. The samples were tested for HCl conversion and EDC selectivity at a reaction temperature of 210° C. and an $O_2/2HCl$ ratio of 0.54. The critical $O_2/2HCl$ ratio was determined as described above.

The samples were tested for HCl conversion and EDC selectivity at a reaction temperature of 210° C. and an $O_2/2HCl$ ratio of 0.54. The critical $O_2/2HCl$ ratio was determined as described above.

TABLE 1

| Cat # | Cu | Mg | K | Na | RE (*) | Fe |
|---|---|---|---|---|---|---|
| 1 | 8.58 | — | 0.55 | — | 0.58 | 0.01 |
| 2 | 9.05 | — | 0.85 | — | 0.45 | 0.02 |
| 3 | 8.00 | — | 0.42 | — | 0.43 | 0.01 |
| 4 | 8.51 | 1.16 | 0.03 | — | 0.45 | — |
| 5 | 8.34 | — | 0.41 | 0.27 | 0.42 | — |
| 6 | 8.24 | 1.21 | 0.03 | 0.28 | 0.41 | — |
| 7 | 10.0 | — | 1.00 | — | — | — |
| 8 | 11.6 | — | — | — | — | — |

(*) Rare earth, a La-rich mixture of rare earth metals.
Amounts of metal are in wt % of the total catalyst (expressed as the metal).

TABLE 2

| Cat # | HCl conversion (%) | EDC selectivity (%) | Critical $O_2$/2HCl ratio (mole/mole) |
|---|---|---|---|
| 1 | 99.9 | 98.7 | <0.52 |
| 2 | 99.0 | 98.6 | <0.54 |
| 3 | 99.6 | 98.7 | <0.50 |
| 4 | 99.9 | 99.3 | <0.52 |
| 5 | 99.8 | 98.8 | <0.54 |
| 6 | 99.9 | 99.2 | <0.56 |
| 7 | 99.8 | 99.0 | <0.56 |
| 8 | 99.5 (*) | <97.0 | (**) |

(*) Measured at $O_2$/2HCl ratio of 0.56. Catalyst did not provide acceptable performance at lower ratios (EDC selectivity unacceptably low).
(**) No stickiness observed at $O_2$/2HCl ratio 0.56. Catalyst did not provide acceptable performance at lower ratios (EDC selectivity unacceptably low).
Only catalysts 1, 3 and 4 meet the criteria of the present invention. Of these three catalysts, catalyst #4 has the highest EDC selectivity and is therefore preferred.
Catalyst #2 is similar to catalyst #1, but has a higher K content, which apparently leads to greater sensitivity to stickiness.
Catalyst #5 is similar to catalyst #1, but contains a small amount (0.27%) of Na. This small amount of Na is sufficient to make catalyst #5 significantly more sensitive to stickiness than is catalyst #1.
Catalyst #6 is similar to catalyst #4, but contains a small amount (0.28%) of Na. This small amount of Na is sufficient to make catalyst #6 significantly more sensitive to stickiness than is catalyst # 4.
Catalyst #7 is a commercially available catalyst. Its sensitivity to stickiness stems from the combination of a relatively high Cu content and the presence of 1% K.
Catalyst #8 is a commercially available catalyst. Its poor HCl conversion and poor EDC selectivity make it unacceptable.

Thus, the invention has been described by reference to certain embodiments discussed above. It will be recognized that these embodiments are susceptible to various modifications and alternative forms well known to those of skill in the art.

What is claimed is:

1. A catalytic oxychlorination process comprising the step of contacting a feed containing an olefin, oxygen, and hydrogen chloride with an oxychlorination catalyst comprising copper, at least one rare earth metal and less than 1 wt % of an alkali metal, in a baffled fluid bed reactor, whereby the $O_2$/2HCl ratio in the feed is in the range of from 0.50 to 0.58.

2. The process of claim 1 wherein the olefin is ethylene.

3. The process of claim 1 wherein the HCl conversion is at least 99.4%, and the process has an EDC selectivity of at least 98.5%.

4. The process of claim 1 wherein the oxychlorination catalyst comprises from 5.5 wt % to 14 wt % copper.

5. The process of claim 4 wherein the oxychlorination catalyst further comprises an alkali earth metal.

6. The process of claim 5 wherein the alkali earth metal is magnesium and wherein the oxychlorination catalyst comprises from 0.2 wt % to 5 wt % magnesium.

7. The process of claim 1 wherein the alkali metal is potassium and wherein the oxychlorination catalyst comprises less than 1 wt % potassium.

8. The process of claim 1 wherein the oxychlorination catalyst comprises from 0.2 wt % to 5 wt % of the at least one rare earth metal.

9. The process of claim 8 wherein the at least one rare earth metal comprises cerium.

10. The process of claim 8 wherein the at least one rare earth metal comprises lanthanum.

11. The process of claim 1 wherein the oxychlorination catalyst further comprises a carrier selected from the group of refractory oxides.

12. The process according to claim 11, wherein the refractory oxide is alumina.

13. The process according to claim 12, wherein the refractory oxide is gamma-alumina.

14. The process of claim 11 wherein the oxychlorination catalyst is prepared in a process comprising co-precipitation of the refractory oxide and a copper compound.

15. The process of claim 11, wherein the oxychlorination catalyst is prepared in a process comprising impregnation of the refractory oxide with an aqueous solution of a copper compound.

16. The process according to claim 15 wherein the copper compound is $CuCl_2$.

17. The process of claim 1, wherein $O_2$/2HCl ratio in the feed is in the range of from above about 0.52 to below 0.56.

* * * * *